United States Patent [19]

Slater

[11] Patent Number: 5,320,636

[45] Date of Patent: Jun. 14, 1994

[54] ENDOSCOPIC SCISSORS INSTRUMENT WITH CAMMED SURFACE END EFFECTORS

[75] Inventor: Charles R. Slater, Fort Lauderdale, Fla.

[73] Assignee: Symbiosis Corporation, Miami, Fla.

[21] Appl. No.: 959,219

[22] Filed: Oct. 9, 1992

Related U.S. Application Data

[63] Continuation-in-part of Ser. No. 780,013, Oct. 21, 1991, Pat. No. 5,203,785, and a continuation-in-part of Ser. No. 680,392, Apr. 4, 1991, Pat. No. 5,192,298.

[51] Int. Cl.$^5$ ............................................. A61B 17/32
[52] U.S. Cl. ................................... 606/205; 128/751
[58] Field of Search ............... 128/749, 751; 606/167, 606/170, 174, 205, 206, 207, 208, 51, 52; 30/183, 184, 186, 188, 189, 266, 194, 221

[56] References Cited

U.S. PATENT DOCUMENTS

| | | |
|---|---|---|
| 523,950 | 7/1894 | Thompson . |
| 1,645,981 | 4/1920 | Benedict . |
| 1,882,218 | 10/1932 | Harvey . |
| 1,947,964 | 2/1934 | Beckmann ............................ 76/104 |
| 1,956,588 | 5/1934 | Parker et al. ........................... 30/13 |
| 2,436,560 | 8/1944 | Feather ................................. 30/266 |
| 2,627,656 | 2/1953 | Richartz ............................... 30/254 |
| 3,376,641 | 4/1968 | Usborne ................................ 30/266 |
| 3,688,402 | 9/1972 | Shannon ............................... 30/260 |
| 3,921,640 | 11/1975 | Freeborn .............................. 128/318 |
| 4,133,107 | 1/1979 | Vogel ................................... 30/266 |
| 4,420,884 | 12/1983 | Hembling ............................ 30/266 |
| 4,950,273 | 8/1990 | Briggs ............................. 606/205 X |
| 5,035,248 | 7/1991 | Zinnecker ...................... 606/205 X |
| 5,069,872 | 12/1991 | Penoza ................................. 420/436 |
| 5,219,357 | 6/1993 | Honkanen et al. ................. 606/205 |

Primary Examiner—Lee S. Cohen
Assistant Examiner—Samuel Gilbert
Attorney, Agent, or Firm—David P. Gordon

[57] ABSTRACT

An endoscopic surgical scissors instrument is provided with end effectors having arcuate cammed surfaces proximal their pivot points. The instrument includes a pair of scissor blades coupled to a pivot post such that at least one blade is pivotally movable with respect to the other from an open position to a closed position. The blades have inside cutting edges which engage each other in bearing contact as the blades are moved from the open to the closed position. In addition, each blade is bowed so as to effect a biasing of the cutting edges together in positions near the closed position. The arcuate cammed surface on the blades are located behind the pivot post, and the cammed surfaces push the blades apart behind the pivot post, thereby urging the cutting edges in front of the pivot post together in the open position of the blades. The cammed surfaces are arranged so that they exert a progressive biasing of the cutting edges together with the most biasing when the blades are in the open position and the least biasing when the blades are in the closed position. By requiring the cams to be arcuate, the cams contact each other in many locations as they slide over each other, thereby reducing wear and increasing stability.

21 Claims, 5 Drawing Sheets

ENDOSCOPIC SCISSORS INSTRUMENT WITH CAMMED SURFACE END EFFECTORS

This application is a continuation-in-part of Ser. No. 780,013, filed Oct. 21, 1991, now U.S. Pat. No. 5,203,785, and Ser. No. 680,392, filed Apr. 4, 1991, now U.S. Pat. No. 5,192,298, the complete disclosures of which are incorporated herein by reference.

BACKGROUND OF THE INVENTION

The invention relates to endoscopic instruments. More particularly, the invention relates to an endoscopic scissors instrument with a cammed biasing surface between scissor blades whereby the cutting edges of the scissor blades are variably biased together as the scissor blades pivot with respect to each other.

Various kinds of scissors are well known in the art. Scissors generally consist of a pair of scissor blades each having an internal cutting edge and a pivot means whereby at least one of the scissor blades pivotally engages the other scissor blade such that its inside cutting edge engages the inside cutting edge of the other scissor blade in bearing contact from a point near the pivot means to a point along the cutting edges distal from the pivot means. In order to effect a smooth cutting action, the engaging cutting edges must be kept in a single moving point of close contact throughout the pivoting of the blades. Continuous close contact of the cutting edges is usually accomplished two ways: first, by biasing the blades together at the pivot means; and second, by constructing the blades with a bowed profile. Prior art FIGS. 1a-1e show an example of this construction.

FIGS. 1a and 1b show a prior art scissors 101 having a first scissor blade 102 and a second scissor blade 104. Each blade has an inside cutting edge 106, 108 and the blades are pivotally joined at a pivot means 110. The blades pivot one with respect to the other, or both with respect to each other, about pivot means 110 from an open position shown in FIG. 1a to a closed position shown in FIG. 1b. Cutting is effected at the bearing contact of one cutting edge with respect to the other as shown by the circled area 112 in FIG. 1a. As will be appreciated, this bearing contact 112 moves from a point near the pivot means 110 as shown in FIG. 1a along the length of cutting edges 106, 108 to a point 114 shown in FIG. 1b as the blades pivot from the open position shown in FIG. 1a to the closed position shown in FIG. 1b.

In order that the cutting action of the scissors be smooth and consistent throughout the movement of the bearing contact from one position to another the cutting edges 106, 108 must be biased together in a direction parallel to the axis of the pivot means 110. Biasing the cutting edges together when the bearing contact 112 is near the pivot means 10 is usually accomplished by providing the pivot means with a biasing member. For example, pivot means 110 is often threaded with a tightening nut or the like which supplies a biasing force which presses the blades together. In actual practice, most hand operated scissors are relatively loose in the open position and the user manually biases the bearing contact by manipulation of the handles. The biasing force applied at the point of pivot means 110 has little effect, however, in biasing the cutting edges together at the point of bearing contact 114 (FIG. 1b) when the blades are pivoted to the closed position.

In order to effect a sufficient biasing of the blades together at bearing contact 114 and throughout the bearing contacts from 112 to 114, the blades are constructed with a slightly bowed profile. FIG. 1c shows a top view of blades 102 and 104 illustrating their respective bowing towards each other. While it will be generally appreciated how this bowing of the blades serves to bias their cutting edges together as the blades pivot towards the closed position, FIGS. 1d and 1e further illustrate this by showing a top view of the blades when the bearing contact 112 is close to the pivot means (FIG. 1d) and a top view of the blades when the bearing contact 114 is furthest from the pivot means (FIG. 1e).

This conventional construction of a scissors is normally quite acceptable. Generally, the bowing of the blades provides reliable biasing of the cutting edges at bearing contact points distant from the pivot means because the blades are tempered and their bowed profile remains relatively constant throughout the life of the scissors. The primary problem with conventional scissors relates to the biasing of the cutting edges together when the blades are in the open position. The open position biasing relies on the biasing means which is subject to wear and eventual loosening resulting in a failure to bias the cutting edges together when the bearing contact of the cutting edges is at position 112 near the pivot means 110. In addition, the biasing provided by the bowing of the blades when the scissors is in the closed position further operates to loosen the biasing at the pivot means since the biasing at the pivot means continues constantly throughout the movement of the blades from the open to the closed positions. Eventually, the user is forced to compensate greatly for this failure of the scissors, and at some point the scissors is deemed inoperable. An additional problem with conventional scissors is that they often do not provide an even feel over the entire cutting range.

These disadvantages are most problematic in small scissors, and in precision cutting scissors such as surgical scissors. In these types of scissors it is important that the blades move smoothly and evenly throughout the entire cutting range. In addition, the problems of the prior art scissors are magnified in small endoscopic scissor instruments. In a standard type scissors, the operator's hands can reflexively adjust biasing of the blades in the open position by manipulation of the handle to effect a smooth cutting action, and the operator's hands receive feedback as the scissors pivot through their entire cutting range. In an endoscopic instrument, however, the handles of the instrument are not directly connected to the blades. Rather the handles are used to move an actuator means which pivots the blades. Thus, manipulation of the handles to effect biasing in the open position will be completely ineffective.

Various improvements in standard type scissors have been proposed over the years. Several of these proposed improvements involve the use of cammed surfaces. U.S. Pat. No. 1,956,588 to Parker et al. discloses a scissors having two pairs of cammed surfaces in the vicinity of the pivot screw. The scissors disclosed by Parker et al. are "detachable blade scissors" where the blade edges are fine and wire-like and are detachable from the blades. When moving such scissor blades from the wide open position towards a closed position, there is a possibility that the detachable blade edges will cross each other preventing closing of the scissors which is quite the opposite from the problem described above where the cutting edges need to be brought closer together when in the open position. In order to prevent the removable blade edges from crossing, cams are provided on the inner surfaces of the blades so that as the blades are moved from the wide open position towards the closed position, the cams ride up on each other and force the blades apart on the cutting side of the pivot screw in the vicinity where the cutting edges are about to meet. Moreover, since these scissor blades are not bowed, biasing of the cutting edges together throughout the shearing stroke is encouraged by another pair of cammed surfaces on the inside surface of the blades which bias the blades apart behind the pivot screw as the blades are closed.

U.S. Pat. No. 2,627,656 to Richartz also discloses a scissors formed without a bowed profile where each blade is provided with a cam-like bearing face on the inside face of the blade behind the pivot axis. The cams are shaped so that their height increases from their ends to their center so that the high points of the cams are in contact when the blades are in the closed position. These cams take the place of the bowing of the blades and force the blades together as they are closed. Richartz does not provide any means for biasing the cutting edges together when the blades are in the open position. U.S. Pat. No. 4,420,884 to Hembling similarly discloses a non-bowed scissors which are constructed of sheet metal stock and coined in a die assembly to form a control cam which biases the cutting edges of the blades together in place of bowing. Also, U.S. Pat. No. 3,688,402 to Shannon discloses a disposable surgical scissors which have camming surfaces in the vicinity of the pivot screw which bias the cutting edges together as they are moved from the open to the closed position in a manner similar to the scissors disclosed by Richartz and Hembling.

U.S. Pat. No. 4,133,107 to Vogel discloses a scissors with a bearing dimple on the inside face of one blade behind the pivot screw and a mating hole on the other blade. This dimple constantly biases the cutting edges together while the blades are moved from the open position to the closed position and vice versa, but does not bias the cutting edges in the wide open position or in the fully closed position.

U.S. Pat. No. 3,376,641 to Usborne discloses scissors and shears where the inner face of each blade has a shoulder. The shoulders protrude from each face at the same distance as each other from the handle side of the pivot, with the face of each shoulder obliquely transverse of the blade and rising in the direction away from the cutting edge. The transverse obliquity of the shoulders ensures that the inside faces of the blades are mutually oblique behind any point of contact of the cutting edges, thus providing clearance or relief of one blade from the other behind its cutting edge. Usborne teaches controlling the blade positions at all stages between fully open and fully closed by providing the shank of each blade, over a length embracing the shoulder, with a back edge shaped such that progressive contact is made between the two shaped edges, and each such contact is always in a substantially straight line that intersects the pivot axis and the corresponding point of contact between the cutting edges of the blades. Accordingly, as the blades of Usborne's scissors are moved from the open to the closed position, the point of contact between the back edges moves away from the pivot point. While Usborne's scissors seem to provide biasing of the cutting edges together near the pivot point when the blades are open, the geometry of Usborne's shoulders and back edges is complex. Usborne's scissors require that there be a substantial shank on each blade, that is, that there be a significant length of blade behind the pivot point leading to the handle. Moreover, as Usborne's biasing resides specifically on a single moving point or a single line of points, the blades are subject to undue wear on that line of points. Thus, Usborne's scissors are not particularly adaptable for use with endoscopic surgical scissors. The geometry is too complex for such small scissors, and the biasing means requires a substantial shank or tang on each blade behind the pivot point and there is no room for such on the end effector of an endoscopic tool. Even if the geometry could be arranged on such small scissors, with a moving point of contact, the tiny shanks would quickly wear and become unreliable.

SUMMARY OF THE INVENTION

It is therefore an object of the invention to provide an endoscopic surgical scissors with an improved biasing means which biases the cutting edges of the blades together near the pivot point of the blades.

It is also an object of the invention to provide an endoscopic surgical scissors with a biasing means which biases the cutting edges of the blades of the scissors together in a progressively decreasing manner as the blades are pivoted from an open to a closed position.

It is another object of the invention to provide an endoscopic surgical scissors with a biasing means which may be adjusted during manufacturing to exert a preselected force.

It is a further object of the invention to provide an endoscopic surgical scissors which utilizes biasing means of the scissor blades in order to generate an even feel throughout the cutting range of the scissors.

In accord with these and other objects of the invention, the endoscopic surgical scissors of the present invention generally comprises a hollow tube, an actuation means having means extending through the hollow tube, a pivot means coupled to the hollow tube, a pair of bowed scissor blades having cutting edges, with at least one of the scissor blades coupled to the actuation means and pivoting around the pivot means, wherein both scissor blades have an arcuate cammed surface located behind the pivot means which contact each other and decreasingly bias the cutting edges of the blades toward each other as the scissor blades pivot with respect to each other from an open to a closed position. Each of the scissor blades of the endoscopic surgical scissors has an inside cutting edge which engages the other cutting edge in bearing contact as the blades are moved from the open to the closed position. The bowing of the blades effects an increased biasing of the cutting edges together as the blades progress from an open to a closed position. On the other hand, the cammed surfaces on the blades effect a decreasing biasing of the cutting edges together as the blades progress from the open to the closed position; i.e., the cammed surfaces are arranged so that they push the blades apart behind the pivot means so as to urge the cutting edges in front of the pivot means together when the blades are in an open position, and so that they progressively decrease the amount by which they push the blades apart behind the pivot means as the blades continue toward the closed position.

Since the cammed surfaces of the blades are arranged to engage each other, the arcuate configuration of the cammed surfaces are arranged to follow the pivotal movement of the blades The cammed surfaces may be configured as protruding ramps of constant slope, or a ramp and corresponding mating recess of constant slope.

Additional objects and advantages of the invention will become apparent to those skilled in the art upon reference to the detailed description taken in conjunction with the provided figures.

DETAILED DESCRIPTION OF THE PREFERRED EMBODIMENT

Figure 2:
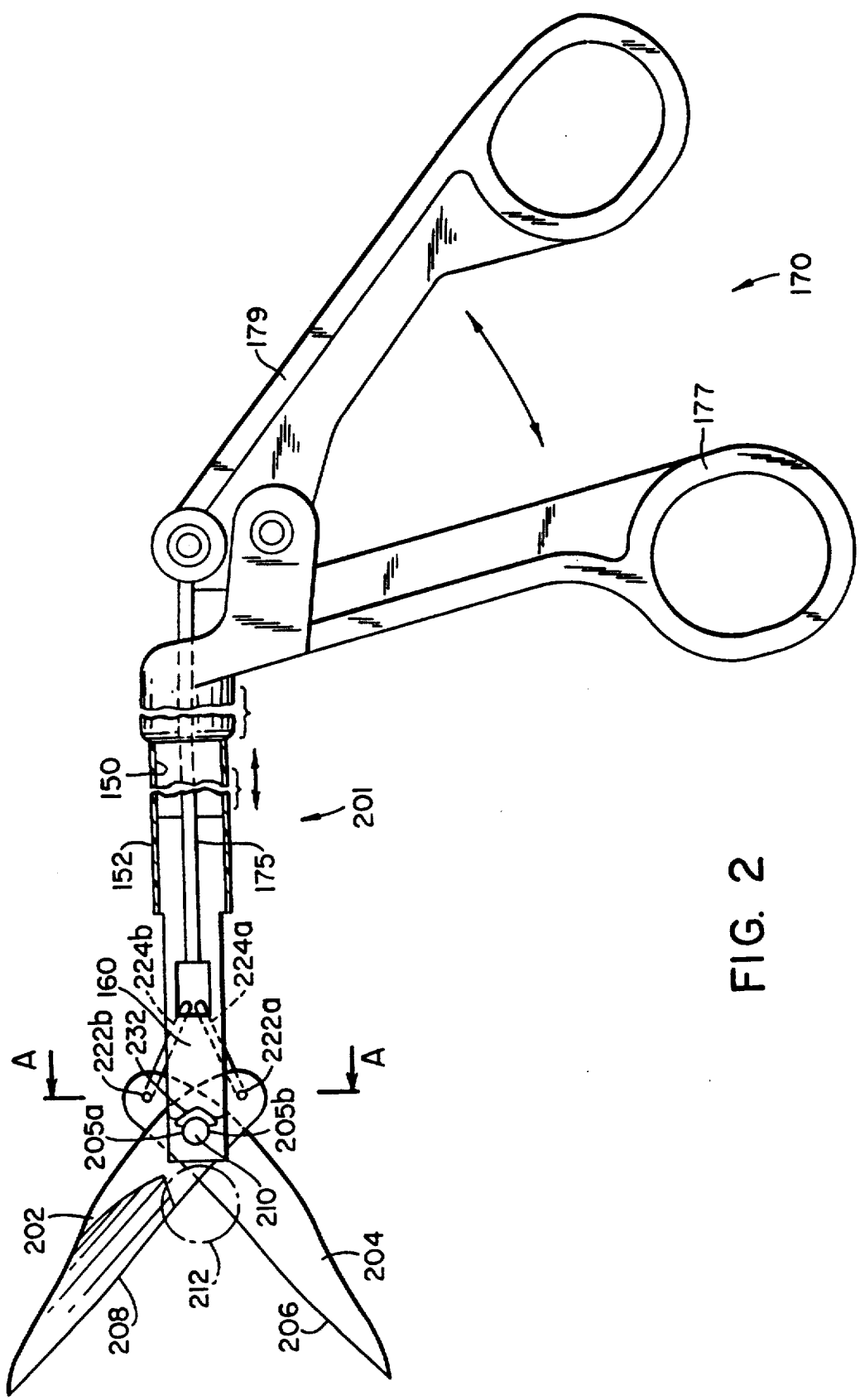
FIG. 2 is a side view of an endoscopic surgical scissors incorporating one embodiment of the invention.

Referring now to FIG. 2, an endoscopic scissors instrument 201 is shown. In the preferred embodiment, the endoscopic scissor instrument comprises a hollow tube 150 surrounded by a peripheral insulating shrink wrap layer of plastic 152, a clevis means 160, an actuating mechanism 170 including a push rod 175 and actuating handle means 177, 179, and cammed scissor blades 202 and 204. In the preferred embodiment of the invention, the handle means 177, 179 pivot relative to each other, with a first of the handle means 177 being coupled to the proximal end of the hollow tube 150, and the second of the handle means 179 being coupled to the proximal end of the push rod. For purposes herein, the "distal end" of the instrument 201 or any part thereof, is the end closest to the surgical site and distant from the surgeon, while the "proximal end" of the instrument 201 or any part thereof, is the end most proximate the surgeon and distant the surgical site. As seen in FIG. 2, the push rod 175 extends through the hollow tube and through a hole in the clevis means 160. The proximal end of the clevis means 160 is fit inside the hollow tube 150, and the clevis means 160 includes a distal post 210 which is transverse the longitudinal axis of the push rod 175 and hollow tube 150. The push rod 175 is coupled to the scissor blades 202, 204 via coupling elements 224a, 224b or the like. The scissor blades 202 204 include holes 205a, 205b which rotatingly surround the post 210. In this manner, when the actuating handle 179 is moved relative to handle 177, the push rod 175 is moved relative to the hollow tube 150, there by causing scissor blades 202, 204 to rotate around the clevis post 210. Additional details of the hollow tube 150, the clevis means 160, and the actuating mechanism 170 may be obtained by reference to parent application Ser. No. 07/680,392. It will also be appreciated that other actuating mechanisms and other mechanisms for causing rotation of the scissor blades could be utilized for the endoscopic cammed scissors instrument of the invention. Indeed, rather than using a clevis with a post around which the scissor blades rotate, the scissor blades could be provided with arcuate grooves as disclosed in U.S. Pat. No. 4,712,545 to Honkanen.

While the invention applies to single acting and double acting endoscopic surgical scissors, each of blades 202, 204 is provided with an inside cutting edge 206, 208. As aforementioned, in the preferred embodiment, blades 202 and 204 are pivoted around a post 210 by movement of an actuation mechanism including the push rod 175 and the coupling elements 224a, 224b, with the coupling elements extending through holes 222a, 222b in the proximal ends of the scissor blades 202, 204. It will be appreciated by those skilled in the art, that other mechanisms for linking the actuation mechanism to the end effectors may be utilized, such as links and pins (disclosed in copending Ser. No. 07/780,014 which is hereby incorporated by reference herein), or a pin riding in cammed slots (as manufactured by U.S. Surgical Corporation, Norwalk, Conn.). Indeed, if desired, in a single acting instrument, the push rod could be directly connected to the scissor blade, and in double acting instruments, two connected push rods could be utilized for direct connection to the scissor blades.

The scissors 201 pictured in FIG. 2 are shown in the open position where the inside cutting edges 206, 208 of blades 202, 204 are in bearing contact near the pivot means 210 at a point shown generally by the circled portion 212. In accord with the invention, cutting edges 206, 208, are biased together at the point 212 by a biasing means 232 on the facing surfaces of blades 202, 204 on the proximal side of the pivot post 210. The biasing means 232 of the invention is shown in greater detail in FIGS. 2a–2e.

Figure 1A:
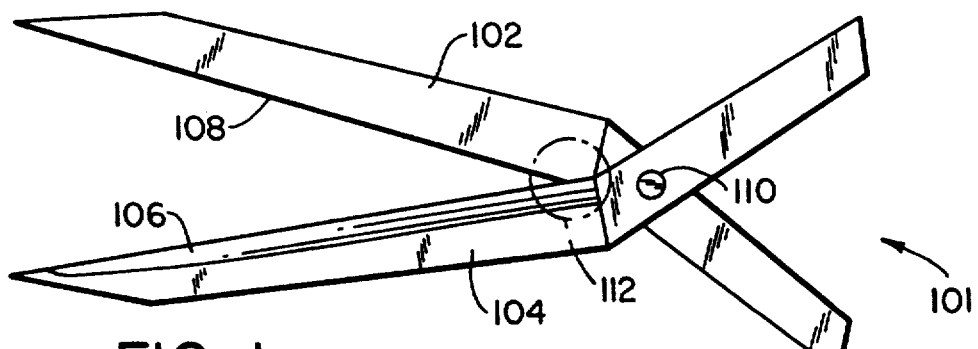
FIG. 1a is a side view of conventional prior art scissors in an open position.
Figure 1B:
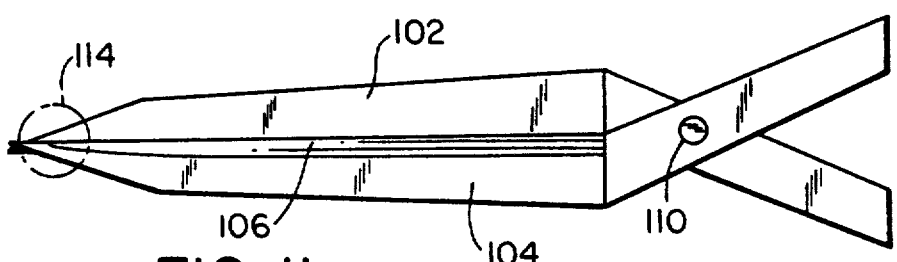
FIG. 1b is a side view of conventional prior art scissors in a closed position.
Figure 1C:
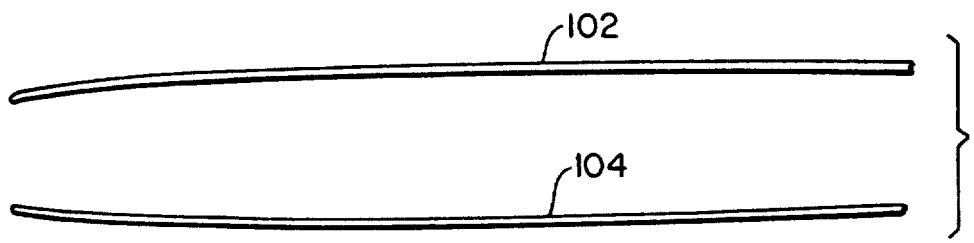
FIG. 1c is a top view of individual conventional prior art scissor blades.
Figure 1D:
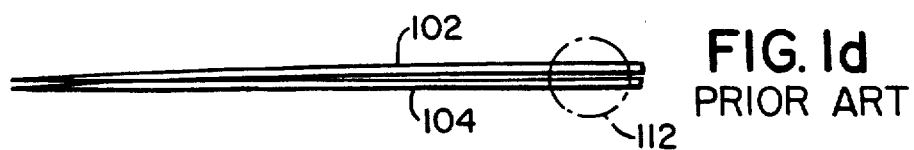
FIG. 1d is a top view of conventional prior art scissors in an open position.
Figure 1E:
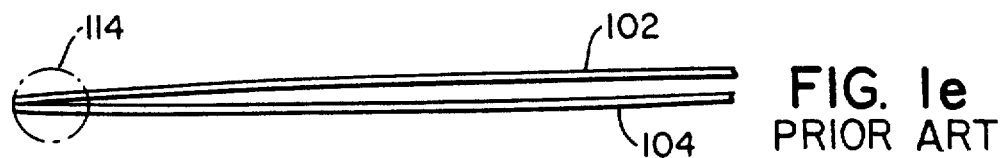
FIG. 1e is a top view of conventional prior art scissors in a closed position.
Figure 2A:
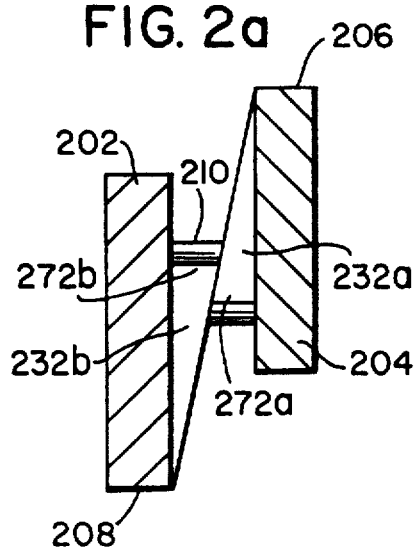
FIGS. 2a and 2b are cross sectional views along line A—A of FIG. 2 with the scissor blades in open and closed positions respectively.
Figure 2B:
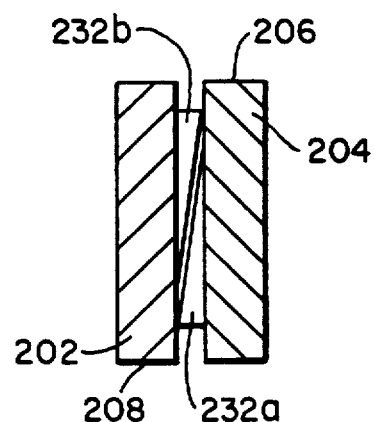
Figure 2C:
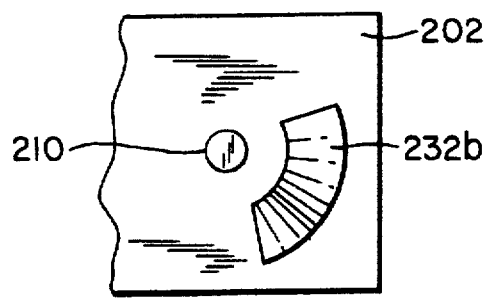
FIGS. 2c is an enlarged side view of a portion of one of the scissor blades of FIG. 2 looking parallel to the pivot axis.
Figure 2D:
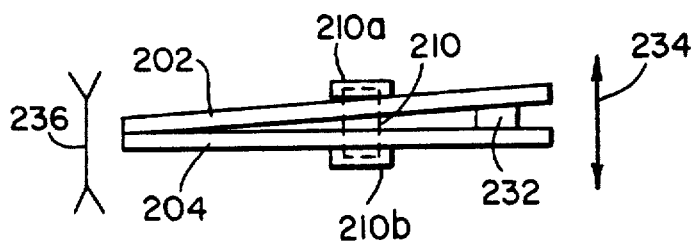
FIGS. 2d and 2e are top views of a portion of FIG. 2 with the scissors in open and closed positions respectively.
Figure 2E:
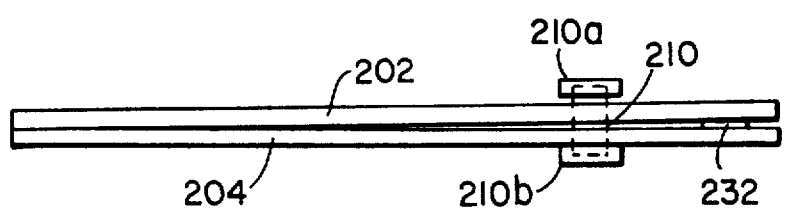

FIGS. 2a and 2b show a cross sectional view of blades 202, 204 along the line A—A of FIG. 2 when the blades 202 and 204 are in open and closed positions respectively, while FIGS. 2d and 2e show a top view of the blades in the same open and closed positions. In the preferred embodiment of the invention, as shown in FIGS. 2a and 2b, the biasing means 232 comprises a pair of cams 232a, 232b on the facing surfaces of blades 202, 204 between the proximal ends of the blades and the pivot post 210. These are shown in greater detail in FIG. 2c. Comparing FIGS. 2a and 2d with FIGS. 2b and 2e, it is seen that when blades 202, 204 are pivoted to the open position (as indicated by FIG. 2a and 2d), the inclined surfaces (cams) 232a and 232b of the biasing means 232 engage each other with the maximum height portions 272a, 272b of the cams in contact with each other. Thus, maximum biasing of the blades 202, 204 forward the pivot 210 is accomplished when the blades are in an open position. However, when the blades 202, 204 are pivoted to the closed position (as indicated by FIGS. 2b and 2e), almost the entire surface of the cams 232a and 232b are engaging each other. In the closed position, the cams establish a minimum biasing of the blades 202, 204 forward the pivot 210. The biasing required for cutting is provided instead by the springiness of the bows of the blades (see FIG. 1e).

Between the fully open and fully closed positions, it will be appreciated that the cams 232a, 232b slide along each other with their surfaces contacting. Thus, it will be appreciated that the amount of biasing is progressively increased as the blades are moved from the closed to the open position and progressively decreased as the blades are moved from the open to the closed position. Also, because the cams are preferably arcuate in shape, with the pivot post 210 acting as the center of the arc, as the cams slide along each other from the open to the closed position, the area or points of contact between the cams increases. The provision of many points of contact not only stabilizes the scissors, but limits the wear on the scissors. At the same time, care must be taken to manufacture the cam surfaces to a fine finish so that friction between the cams does not inhibit the functioning of the scissors.

FIG. 2c shows an enlarged side view of a portion of one of the blades 204 in the vicinity of pivot means 210. Here it can be seen that cam 232a is arranged in an arc concentric with the axis of pivot means 210. Cam 232b is configured in an identical manner. Ideally, the arcs of the cams 232a, 232b circumscribe an angle of approximately 60 degrees ($\pi/3$ radians), although this may vary depending on other design considerations when the scissors are constructed. Moreover, it is presently preferred that the arc have as large a radius as possible; i.e. that the cams be placed as far back away from the pivot means as possible. Again, however, this may vary depending on other design considerations when the scissors are constructed. Also, in the preferred embodiment, the angle of incline of cams 232a and 232b is small (e.g., about one degree), although it will be appreciated that other angles could be utilized.

Turning to FIGS. 2d and 2e, it is seen that clevis post 210 is preferably provided with some mechanism such as caps 210a, 210b to prevent more than a predetermined amount of lateral movement of blades 202, 204 apart from each other. Different mechanisms for preventing lateral movement of the blades such as, e.g., a rivet, a screw and nut, etc., are well known in the art. As can be appreciated from FIG. 2d, the biasing of blades 202, 204 apart from each other by the biasing means 234 on the proximal side of pivot post 210 in the direction of arrows 234 results in a corresponding biasing together of cutting edges 206, 208 in the direction of arrows 236 on the distal side of pivot post 210.

Figure 3A:
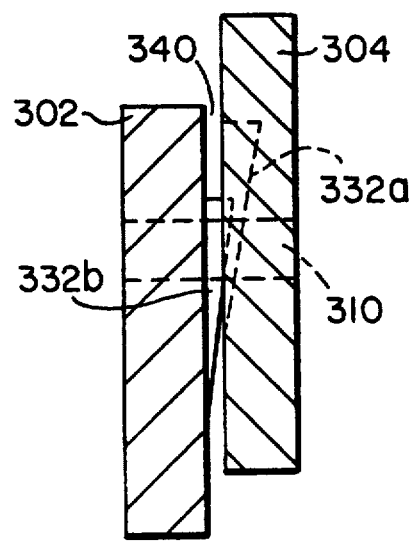
FIGS. 3a and 3b are views similar to FIGS. 2a and 2b but showing another embodiment of the invention with scissor blades in the opened and closed position respectively.
Figure 3B:
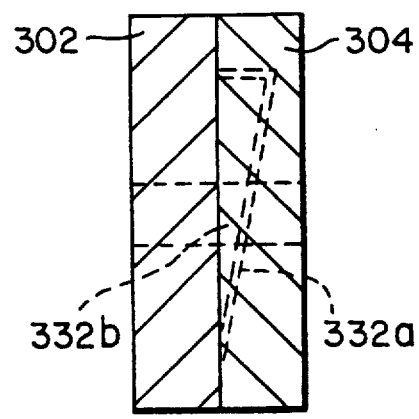

Turning to FIGS. 3a and 3b, a second embodiment of the invention is seen with a first scissor blade 304 provided with an inclined cam 332a while the second scissor blade 302 is provided with an inclined recess 332b. FIG. 3a shows the positions of the cam 332a and recess 332b when the blades 302, 304 are in the open position, and FIG. 3b shows the positions of the cam 332a and recess 332b when the blades 302, 304 are in the closed position It will be appreciated that in the embodiment of FIG. 2, the blades 202, 204 are always spaced apart a minimal distance substantially equivalent to the maximum height of inclined cam 232a (232b), and that in the open position, the spacing between the proximal ends of the blades is substantially twice the height of the maximum height of the inclined cam. In the embodiment of FIGS. 3a and 3b, however, it is possible to minimize the minimal distance (FIG. 3b) that the blades are spaced apart when in the closed position. Nevertheless, it is presently preferred to use the embodiment of FIG. 2 and to always keep at least some minimal distance between the blades even when in the closed position so as to reduce friction.

In both embodiments of the cams and the cam and recess, and as aforedescribed, it is desirable that the entire surface or substantially the entire surface of each biasing member contact substantially the entire surface of the other biasing member when the scissors are in the closed position. As the scissors are moved to the open position, the surface area of their contact decreases progressively. However, numerous points of contact remain. Thus, a biasing surface is established which is less subject to wear than that of the prior art. By finely finishing the cam surfaces, smooth operation is guaranteed.

Having described and illustrated several different embodiments of an endoscopic scissors having cammed surfaces, it will be appreciated with the knowledge and understanding of the principles disclosed herein that the cammed surface biasing means must be properly dimensioned relative to the overall dimensions of the scissors to effect the appropriate amount of biasing and the appropriate progression towards biasing as the scissor blades are pivoted from the closed to the open position. In other words, the location and angle of the cammed surfaces are chosen based on the amount of biasing desired from cammed surfaces of the scissors. The amount of bias, in turn, is at least partially dictated by the amount of bias provided by the springy bows in the blades, which is dictated by the extent of the bows and the materials utilized. Thus, if it is desired to maintain an even cutting feel to the endoscopic scissors, the biasing force accomplished by the cammed surfaces in the fully open position (where biasing due to the bow in the blade is typically zero) should be approximately equal to the biasing force accomplished by the bowed blades in the fully closed position (where biasing due to the cammed surfaces is nominally zero. With this in mind, it will be appreciated that numerous configurations may have to be made before one skilled in the art arrives upon a final suitable configuration. However, if the blades of the scissors are made via casting or stamping techniques, as is the preferred manner of making the blades of the invention, a large cost will be incurred in providing numerous molds or dies for casting or stamping numerous blade configurations.

Figure 4A:
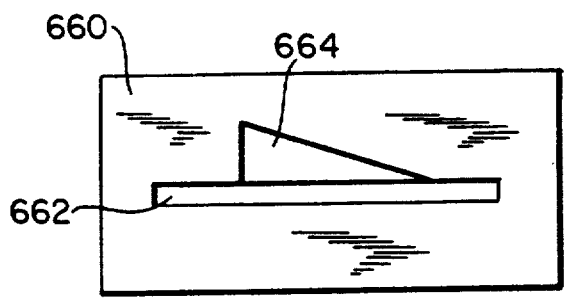
FIGS. 4a-4c schematically show a progressive mold which can be used to construct the cammed scissor blades of the invention.
Figure 4B:
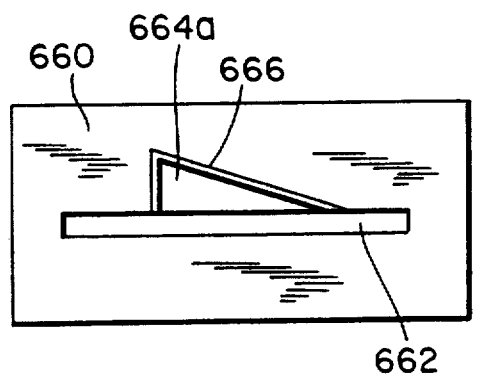
Figure 4C:
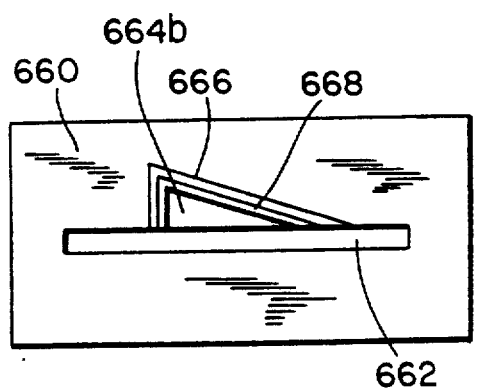

In accord with another aspect of the invention, in order to eliminate the costs of providing numerous molds or dies for casting or stamping numerous blade configurations, a progressive casting or stamping arrangement is provided. An example of such an arrangement is shown in FIGS. 4a-4c. FIG. 4a shows a cross section of a portion of a mold or die 660 used to cast endoscopic scissor blades in accord with the invention. Mold or die 660 has a blade cavity 662 and an adjacent cam cavity 664. As shown in FIG. 4a, cam cavity 664 is a certain size and shape. In order to optimize the size/-shape of the cam formed in cam cavity 664, inserts 666, 668, may be applied to the mold or die 660 as shown for example in FIGS. 4b and 4c. FIG. 4b shows one insert 666 inserted into cam cavity 664 of FIG. 4a resulting in a cam casting or die cavity 664a of reduced size and optionally different shape. Similarly, the cam or die cavity may be further modified by the addition of a second insert 668 resulting in an even smaller cam casting or die cavity 664b shown in FIG. 4c. Inserts may be numerous and of various shapes as well as various sizes so that the same cast or die 660 may be used to produce a number of blades with different cams by the addition or deletion of inserts. It will be appreciated by those skilled in the art that the mold or die inserts 666, 668 are held in the mold or die according to the practice common for assembling portions of injection molds or dies. Typically, such a practice includes utilizing pins, keys, undercuts, etc., as desired.

There have been described and illustrated herein endoscopic scissors instruments having scissor blades with cammed surfaces. While particular embodiments of the invention have been described, it is not intended that the invention be limited thereto, as it is intended that the invention be as broad in scope as the art will allow and that the specification be read likewise. Thus, while the endoscopic surgical scissors shown for exemplary purposes were double acting scissors where both blades pivot relative to each other, it will be recognized that the invention can be applied to a single acting scissors with one blade fixed and the other blade pivoting relative to the fixed blade. Also, while particular actuation mechanisms were described for causing the pivoting of the scissor blades, it will be appreciated that other mechanism could be utilized. It will therefore be appreciated by those skilled in the art that yet other modifications could be made to the provided invention without deviating from its spirit and scope as so claimed.

I claim:

1. Endoscopic scissors instrument comprising:
   a) a hollow tube having a proximal end and a distal end;
   b) a first scissor blade having a proximal portion, a distal portion, and rotational means for permitting said first scissor blade to rotate, said first scissor blade having a leading edge, said leading edge having a first inside cutting edge on said distal portion of said first scissor blade, and said first scissor blade having a first facing surface on said proximal portion of said first scissor blade, said first facing surface having first inclined camming means for biasing said first scissor blade, said first inclined camming means increasing in thickness as it extends away from said leading edge, said first inclined camming means extending in an arc of a first radius and having a first incline;
   c) a second scissor blade having a proximal portion and a distal portion, said second scissor blade having a second leading edge having a second inside cutting edge on said distal portion of said second scissor blade, and said second scissor blade having a second facing surface on said proximal portion of said second scissor blade, said second facing surface having a second inclined camming means for biasing said second scissor blade, said second inclined camming means increasing in thickness as it extends away from said second leading edge, said second inclined camming means extending in an arc in a second radius substantially equal to said first radius and having a second incline substantially identical to said first incline, and said first and second scissor blades being laterally offset from each other; and
   d) actuating means extending through said tube for causing said first scissor blade to pivot from an open position toward a closed position, wherein when said first scissor blade pivots from said open position toward said closed position, said inside cutting edge of said first scissor blade contacts said inside cutting edge of said second scissor blade in a bearing contact starting at a first point and moving distally therefrom to effect a cutting action, and said first camming means increasingly contacts said second camming means and decreasingly biases said facing surfaces.

2. Endoscopic scissors instrument according to claim 1, further comprising:
   pivot means for allowing said first scissor blade to pivot, said pivot means coupled to said distal end of said hollow tube, wherein
   said first scissor blade has a first hole,
   said pivot means extends through said first hole, and
   said actuating means causes said first scissor blade to pivot around said pivot means.

3. Endoscopic scissors instrument according to claim 2, wherein:
   said second scissor blade has a second hole between said proximal and distal portion of said second scissor blade, with said pivot means extending through said second hole, and said actuating means coupled to said second scissor blade for causing said second scissor blade to pivot around said pivot means.

4. Endoscopic scissors instrument according to claim 3, further comprising:
   first coupling means for coupling said actuating means and said first scissor blade, wherein said first scissor blade includes a third hole proximal said first hole receiving said first coupling means; and
   second coupling means for coupling said actuating means and said second scissor blade, wherein said second scissor blade includes a fourth hole proximal said second hole receiving said second coupling means.

5. Endoscopic scissors instrument according to claim 4, wherein:
   said first scissor blade and said second scissor blade are bowed,
   said arc of said first inclined camming means has said first radius extending from said pivot means,
   said arc of said second inclined camming means has said second radius extending from said pivot means, and
   said first inclined camming means and said second inclined camming means have finely ground surfaces.

6. Endoscopic scissors instrument according to claim 5, wherein:
   said first inclined camming means comprises a first cam projecting from said first facing surface, and
   said second inclined camming means comprises a second cam projecting from said second facing surface.

7. Endoscopic scissors instrument according to claim 2, further comprising:
   coupling means for coupling said actuating means and said first scissor blade, wherein said first scissor blade includes another hole proximal said first hole receiving said coupling means.

8. Endoscopic scissors instrument according to claim 1, wherein:
   said first scissor blade and said second scissor blade are bowed.

9. Endoscopic scissors instrument according to claim 8, wherein:
   said bowed blades and said first and second camming means provide said endoscopic scissors instrument with a first biasing force when said bowed blades are substantially closed, and said first camming means and said second camming means provide said endoscopic scissors instrument with a second biasing force when said bowed blades are substantially open, and said first biasing force and said second biasing force are substantially equal.

10. Endoscopic scissors instrument according to claim 9, wherein:

aid first and second inclined camming means each have an inclination, said inclinations and the location of said first and second camming means on said first and second facing surfaces are chosen such that said bowed blades have a substantially constant biasing force as they close from said open position to said closed position.

11. Endoscopic scissors instrument according to claim 1, wherein:

said first inclined camming means comprises a first cam projecting from said first facing surface, and said second inclined camming means comprises a second cam projecting from said second facing surface.

12. Endoscopic scissors instrument according to claim 1, wherein:

said first inclined camming means comprises a first cam projecting from said first facing surface, and said second inclined camming means comprises an inclined recess in said second facing surface.

13. Endoscopic scissors instrument according to claim 1, wherein:

said first inclined camming means comprises an inclined recess in said first facing surface, and said second inclined camming means comprises a cam projecting from said second facing surface.

14. Endoscopic scissors instrument according to claim 1, wherein:

said arc of said first inclined camming means has said first radius extending from said pivot means, and said arc of said second inclined camming means has said second radius extending from said pivot means.

15. Endoscopic scissors instrument according to claim 1, wherein:

said first inclined camming means and said second inclined camming means have finely ground surfaces.

16. Endoscopic scissors instrument according to claim 1, wherein:

said first and second inclined camming means each have an inclination of approximately one degree.

17. Endoscopic scissors instrument comprising:

a) a hollow tube having a proximal and a distal end;

b) a movable actuator means extending through said tube;

c) first scissor blade means for cutting, said first scissor blade means having a proximal end, a distal end, an inside cutting edge, rotational means for permitting said first scissor blade means to rotate, and a proximal portion having with a facing surface, said first scissor blade means having cam means for biasing on said facing surface of said first scissor blade means; and d) second scissor blade means for cutting, said second scissor blade means being laterally offset from said first scissor blade means, and having a proximal end, a distal end, an inside cutting edge, and a proximal portion having a second facing surface, said second scissor blade means having second cam means for biasing on said second facing surface of said second scissor blade means, wherein by moving said movable actuator means, said actuator means causes said first scissor blade means to pivot from an open position towards a closed position with said cam means decreasingly biasing said facing surfaces and said inside cutting edges of said first and second scissor blade means engaging each other in a bearing contact starting at a proximal point and moving distally therefrom to effect a cutting action.

18. Endoscopic surgical scissors according to claim 17, further comprising:

pivot means for allowing said first scissor blade means to pivot, said pivot means being coupled to said distal end of said hollow tube, wherein said rotational means of said first scissor blade means includes a first hole through which said pivot means extends, and said actuator means is coupled to said proximal end of said first scissor blade means.

19. Endoscopic surgical scissors according to claim 18, wherein:

said second scissor blade means includes a second hole through which said pivot means extends, and said actuator means is coupled to said proximal end of said second scissor blade means.

20. Endoscopic surgical scissors according to claim 17, wherein:

each of said cam means is arcuate and has a substantially identical radius.

21. Endoscopic surgical instrument according to claim 20, wherein:

each said cam means has a surface, wherein said surface of said cam means of said first scissor blade means substantially a completely contacts said surface of said cam means of said second scissor blade means when said first and second scissor blade means are in a closed position, and the contact surface area between said surfaces progressively decreases as said first and second scissor blade means move toward an open position.

* * * * *